(12) United States Patent
Turner et al.

(10) Patent No.: US 11,866,620 B2
(45) Date of Patent: Jan. 9, 2024

(54) HOTMELT COMPOSITION COMPRISING THREE POLYMERS HAVING DIFFERENT PEAK MOLECULAR WEIGHTS

(71) Applicant: The Procter & Gamble Company, Cincinnati, OH (US)

(72) Inventors: Robert Haines Turner, Cincinnati, OH (US); Torsten Lindner, Kronberg (DE); William L. Bunnelle, Ham Lake, MN (US)

(73) Assignee: The Procter and Gamble Company, Cincinnati, OH (US)

( * ) Notice: Subject to any disclaimer, the term of this patent is extended or adjusted under 35 U.S.C. 154(b) by 258 days.

(21) Appl. No.: 17/075,755

(22) Filed: Oct. 21, 2020

(65) Prior Publication Data

US 2021/0115303 A1 Apr. 22, 2021

Related U.S. Application Data

(60) Provisional application No. 62/923,707, filed on Oct. 21, 2019.

(51) Int. Cl.
| | |
|---|---|
| *C09J 5/06* | (2006.01) |
| *C09J 123/16* | (2006.01) |
| *A61L 15/58* | (2006.01) |
| *B65D 85/07* | (2017.01) |
| *B32B 7/12* | (2006.01) |
| *B32B 5/02* | (2006.01) |
| *B32B 5/26* | (2006.01) |
| *C09J 123/14* | (2006.01) |

(52) U.S. Cl.
CPC ............... *C09J 5/06* (2013.01); *A61L 15/585* (2013.01); *B32B 5/022* (2013.01); *B32B 5/26* (2013.01); *B32B 7/12* (2013.01); *B65D 85/07* (2018.01); *C09J 123/16* (2013.01); *B32B 2307/726* (2013.01); *B32B 2555/02* (2013.01); *C08L 2205/03* (2013.01); *C09J 123/14* (2013.01); *C09J 2423/00* (2013.01); *C09J 2423/16* (2013.01)

(58) Field of Classification Search
CPC . C09J 5/06; C09J 123/16; C09J 123/14; C09J 2423/00; C09J 2423/16; A61L 15/585; B32B 5/022; B32B 5/26; B32B 7/12; B32B 2307/726; B32B 2555/02; B65D 85/07; C08L 2205/03

See application file for complete search history.

(56) References Cited

U.S. PATENT DOCUMENTS

| | | |
|---|---|---|
| 5,599,335 A | 2/1997 | Goldman et al. |
| 5,723,546 A † | 3/1998 | Sustic |
| 6,645,190 B1 | 11/2003 | Olson et al. |
| 6,761,711 B1 | 7/2004 | Fletcher et al. |
| 6,817,994 B2 | 11/2004 | Popp et al. |
| 6,840,928 B2 | 1/2005 | Datta et al. |
| 6,849,067 B2 | 2/2005 | Fletcher et al. |
| 6,893,426 B1 | 5/2005 | Popp et al. |
| 6,953,452 B2 | 10/2005 | Popp et al. |
| 6,969,377 B2 | 11/2005 | Koele et al. |
| 7,156,833 B2 | 1/2007 | Couture-Dorschner et al. |
| 7,201,744 B2 | 4/2007 | Van Gompel et al. |
| 7,262,251 B2 † | 8/2007 | Kanderski |
| 7,497,851 B2 | 3/2009 | Koele et al. |
| 7,682,349 B2 | 3/2010 | Popp et al. |
| 7,744,576 B2 | 6/2010 | Busam et al. |
| 7,862,550 B2 | 1/2011 | Koele et al. |
| 8,007,485 B2 | 8/2011 | Popp et al. |
| 8,361,048 B2 | 1/2013 | Kuen et al. |
| 8,372,052 B2 | 2/2013 | Popp et al. |
| 8,579,876 B2 | 11/2013 | Popp et al. |
| 8,747,379 B2 | 6/2014 | Fletcher et al. |
| 9,421,137 B2 | 8/2016 | LaVon et al. |
| 2006/0024433 A1 | 2/2006 | Blessing et al. |
| 2008/0312617 A1 | 12/2008 | Hundorf et al. |
| 2008/0312622 A1 | 12/2008 | Hundorf et al. |
| 2010/0051166 A1 | 3/2010 | Hundorf et al. |
| 2011/0250413 A1 | 10/2011 | Lu et al. |
| 2011/0268932 A1 | 11/2011 | Catalan et al. |
| 2011/0319848 A1 | 12/2011 | McKiernan et al. |
| 2012/0312491 A1 | 12/2012 | Jackels et al. |
| 2014/0005020 A1 | 1/2014 | LaVon et al. |
| 2014/0072767 A1 | 3/2014 | Klaska et al. |
| 2014/0358100 A1 † | 12/2014 | Remmers |

(Continued)

FOREIGN PATENT DOCUMENTS

| | | |
|---|---|---|
| CN | 109562001 A | 4/2019 |
| CN | 110023440 A | 7/2019 |
| EP | 1447066 B1 | 10/2008 |
| EP | 2905000 B1 | 12/2016 |
| EP | 2905001 B1 | 1/2017 |
| WO | 199410256 A1 † | 5/1994 |
| WO | WO 9511652 A1 | 10/1994 |
| WO | WO 2012052172 A1 | 4/2012 |
| WO | WO 2012170778 A1 | 12/2012 |

(Continued)

OTHER PUBLICATIONS

International Search Report and Written Opinion; Application Ser. No. PCT/US2020/070678; dated Feb. 1, 2021; 13 pages.

*Primary Examiner* — Callie E Shosho
*Assistant Examiner* — Bethany M Miller
(74) *Attorney, Agent, or Firm* — Amanda Herman Berghauer; Daniel Albrecht

(57) ABSTRACT

A hotmelt composition comprises at least three co-polymers defined by their chemistry and molecular weight. The hotmelt composition may be without tackifiers. The hotmelt can be used in absorbent articles such as diapers comprising two substrates at least partially attached by the hotmelt composition. The hotmelt provides especially good nonwoven-nonwoven bond and nonwoven-film bond.

17 Claims, 4 Drawing Sheets

(56) References Cited

U.S. PATENT DOCUMENTS

| | | |
|---|---|---|
| 2016/0053149 A1 | 2/2016 | Herrlich et al. |
| 2017/0204306 A1* | 7/2017 | Wang et al. |
| 2017/0209616 A1* | 7/2017 | Turner ................ A61F 13/5323 |
| 2017/0355841 A1† | 12/2017 | Schauder |
| 2018/0037778 A1 | 2/2018 | Briseno et al. |
| 2018/0282451 A1† | 10/2018 | Carvagno |
| 2019/0060946 A1* | 2/2019 | Ries ......................... B05D 1/28 |
| 2019/0144719 A1* | 5/2019 | Wang ....................... B32B 7/12 |
| | | 156/334 |

FOREIGN PATENT DOCUMENTS

| | | |
|---|---|---|
| WO | WO 2012170798 A1 | 12/2012 |
| WO | WO 2014093323 A1 | 6/2014 |
| WO | WO 2015031225 A1 | 3/2015 |
| WO | WO 2015183669 A1 | 12/2015 |
| WO | WO 2016133712 A1 | 8/2016 |

\* cited by examiner
† cited by third party

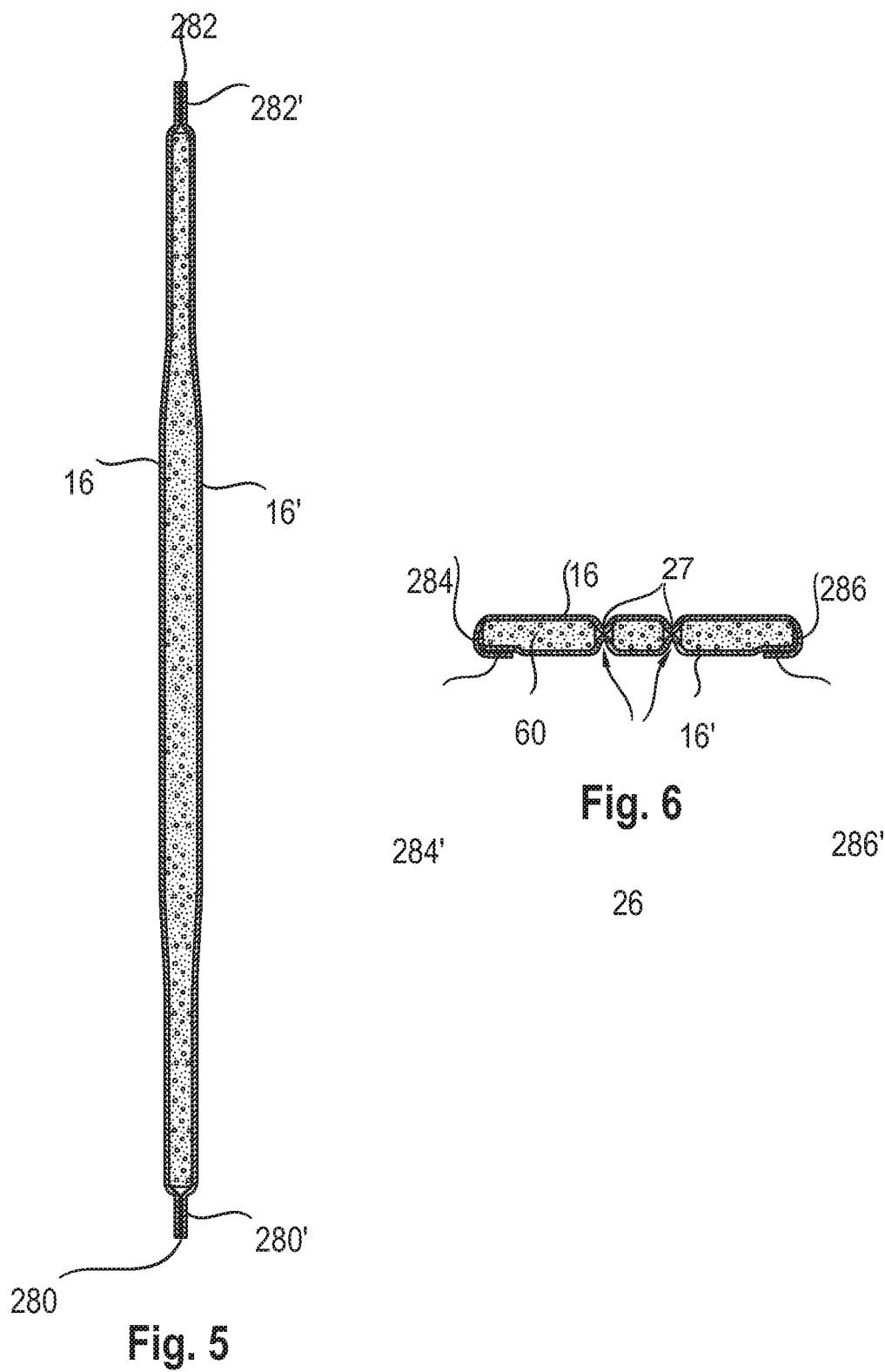

HOTMELT COMPOSITION COMPRISING THREE POLYMERS HAVING DIFFERENT PEAK MOLECULAR WEIGHTS

CROSS REFERENCE TO RELATED APPLICATION

This application is a claims the benefit of U.S. Provisional Application No. 62/923,707, filed on Oct. 21, 2019, which is incorporated herein by reference.

FIELD

The present invention is directed at a hotmelt composition that can be used to bond a first substrate with a second substrate. The hotmelt composition provides especially good nonwoven-nonwoven bonds but can also be used for nonwoven-film bonds. The hotmelt composition is particularly useful in absorbent articles such as diapers. The hotmelt composition may be substantially free of tackifiers.

BACKGROUND

Disposable absorbent articles, such as diapers, training pants or adult incontinence articles, typically comprise a liquid-permeable topsheet, a liquid-impermeable backsheet and an absorbent core located between the topsheet and the backsheet, among other features. The liquid-permeable topsheet is positioned next to the body of the wearer when the disposable article is worn and allows passage of bodily fluids into the absorbent core. The liquid-impermeable backsheet helps prevent leakage of fluids held in the absorbent core. The absorbent core typically comprises superabsorbent polymers (SAP) that can absorb several times their weight of urine or other liquid, so that bodily fluids can be transported and stored from the skin of the wearer into the disposable absorbent article.

The various parts of a disposable absorbent article are bonded together directly or indirectly. For example, hotmelt adhesives have been used to bond individual layers of the chassis of the absorbent article, in particular topsheet, backsheet and absorbent core together. Hotmelt adhesives have also been used to bond other discrete parts, such as fasteners and leg elastics or cuffs, to the chassis of the article. The hotmelt adhesive is often called a construction adhesive because it is used to help construct the absorbent article from individual components. Other bonding means such as fusion bonding and ultrasonic bonding are also used.

Common hotmelt adhesives are made by combining polymers and additive components in a substantially uniform thermoplastic blend. Typical additive components include tackifiers, plasticizers, and/or waxes. While such formulations generally work, they can be costly and their performance properties can be improved. Tackifiers for example can comprise up to 65% of an adhesive formula, and can be expensive and difficult to source.

Instead of using formulated adhesives, unblended polymers have been proposed. An unblended polymer consists only of one type of polymer (generated via its own and specific polymerization process) rather than a blend of polymers which are made via separate polymerization process and mixed (blended) together after polymerization. Unblended polymers may additionally comprise minor amount of additives such as antioxidants, perfumes and other low molecular weight components, but is substantially free of other polymers, mineral oils, or tackifiers.

US 2016/0053149 A1 (Clariant) for example discloses a ready-to-use hotmelt adhesive comprising at least 95% of one or more polyolefin copolymer waxes, which have been prepared by means of metallocene catalysts, characterized in that the polyolefin copolymer wax consists of propylene and one or more further monomers selected from ethylene and branched or unbranched 1-alkenes having 4 to 20 C atoms and the content of structural units derived from propylene in the copolymer waxes amounts to 80 to 99.9% by weight, and the hot melt adhesive has a surface tension of the melt, measured at a temperature of 170° C., of at most 23 mN/m.

Hotmelt adhesives are often applied by slot coating in hygiene absorbent articles, as this ensures a reliable and precise deposition of the hotmelt on a substrate, compared to spray application. Pure polymer adhesives were found difficult to slot coat at higher speed (>2 m/s) without accretion of material building up on the lip of the die and releasing suddenly downstream of the die. In the slot process, the nozzle is in direct contact with the substrate, as it drags over it while the bonding agent is deposited on the substrate. The adhesive leaves the application head via a slit with a typical width of 150 to 250 µm in machine direction. Using such slot applicator nozzles, the inventors observed rapid build-up of pure polymer composition downstream of the slot die nozzle (referred to as "blobbing" or "drooling"), when run at high line speed, typically within a few minutes. This contamination causes line stops after short periods of running time and can lead to consumer-noticeable defects in the product when a larger accumulation ("blob") of the solidified adhesive is incorporated in the product.

There is thus a need for a hotmelt composition that can be applied at a relatively high line speed by a slot coating process without blobbing to bond two nonwoven substrates or a film and a nonwoven substrate, and that may be formulated with low amount or seven free of tackifiers.

SUMMARY OF THE INVENTION

In a first aspect, the invention is for a hotmelt composition comprising:
  a first propylene-ethylene copolymer having a peak molecular weight Mp below 40,000 g/mol;
  a second propylene-ethylene copolymer having a peak molecular weight Mp above 40,000 g/mol; and
  a third polymer having a peak molecular weight Mp of from 70,000 g/mol to 700,000 g/mol, which is at least greater by 10,000 g/mol than the peak molecular weight of the second copolymer.

In a second aspect, the invention is for an absorbent article comprising a first and second substrate bonded to each other by the hotmelt composition and a package comprising a plurality of such articles. In another aspect, the invention is for a process for bonding a first substrate to a second substrate with the hotmelt composition.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 5 shows a longitudinal cross-section view of the absorbent core of FIG. 4;

FIG. 6 shows transversal cross-section view of the absorbent core of FIG. 4;

DETAILED DESCRIPTION

Introduction

Figure 1:
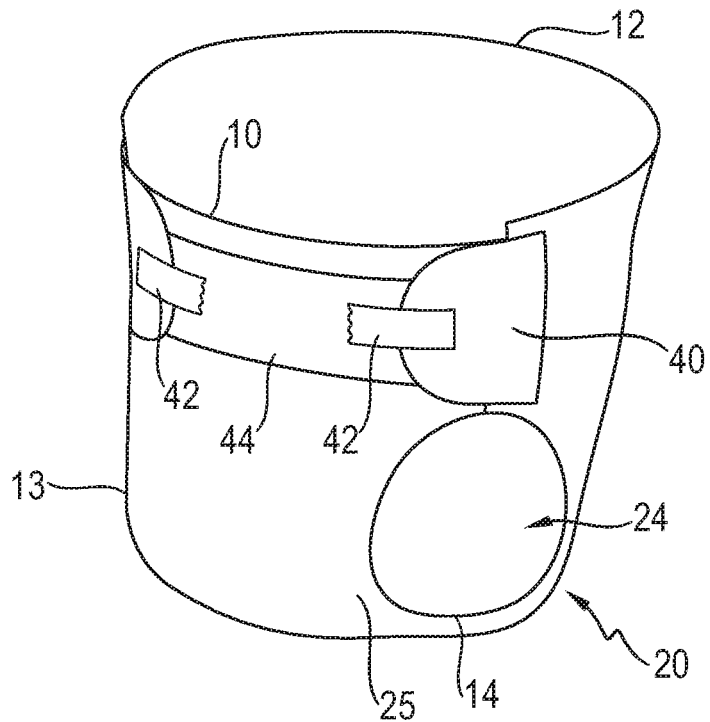
FIG. 1 shows a perspective view of an exemplary taped diaper in a closed configuration as it would be when worn by a wearer.

"Comprise," "comprising," and "comprises", as used herein, are open ended terms, each specifies the presence of what follows, e.g., a component, but does not preclude the presence of other features, e.g., elements, steps, components known in the art, or disclosed herein. Any features indicated below is optional unless indicated otherwise.

The hotmelt composition comprises a first, second and third polymers that are described below.

First Copolymer and Second Copolymer

The first polymer and the second polymer are both propylene-ethylene copolymer and differ in their peak molecular weight Mp, as will be discussed below. The polymers are preferably metallocene-technology based, that is produced using a metallocene catalysts, but other catalysts such as Ziegler Natta could also be used. Metallocene-technology based polymers typically have a regular spatial repeat monomer unit distribution and a narrow molecular weight distribution, as is known in the art.

The first and second propylene-ethylene copolymers comprise at least 50% by weight of propylene unit, in particular at least 60%, or at least 70%, or at least 80% by weight. The remaining monomers are ethylene monomers. optionally other alpha olefin monomers may be present in the co-polymers, for example 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof. The exact monomer distribution is typically published by the supplier, but can also be determined by a suitable method, such as nuclear magnetic resonance or infrared spectroscopies.

Suitable metallocene-technology based propylene-ethylene copolymers are commercially available from Clariant under the polymer range Licocene®, with a broad range of properties such as molecular weight, viscosity, crystallinity, etc. US 2016/0053149 A1 assigned to Clariant also describes suitable co-polymers and on page 5 indicates that these examples were produced by the processes indicated in EP571,882. For a given catalyst system and given comonomer ratio, the molecular weight was regulated via the hydrogen partial pressure as molar mass regulator.

The first copolymer is a propylene-ethylene copolymer having a peak molecular weight Mp below 40,000 g/mol. The hotmelt composition may comprise from 20% to 80% of the first copolymer, or mixtures of such copolymers, in particular from 30% to 70%, or from 40% to 60%. The first copolymer may in particular have a Mp ranging from 4,000 g/mol to 31,000 g/mol, or from 19,000 g/mol to 26,000 g/mol.

The first copolymer may be a single material as defined above, as this simplifies the compounding and formulation of the hotmelt composition, but the first copolymer may also be a mixture of two or more copolymers falling under this definition.

The first copolymer preferably has a low degree of crystalline character, reflected by an enthalpy of fusion of less than 20 J/g, in particular of less than 15 J/g. A commercial example of the first copolymer is Licocene® PP 1302, from Clariant. Licocene® PP 1302 is sold as granules and is described as a low melting, metallocene-technology based propylene-ethylene copolymer wax, which exhibits a low degree of crystallinity. The Mp of Licocene® PP 1302 was measured to be 24,100 g/mol and its enthalpy of fusion of 11.8 J/g (see measurement method below).

The second copolymer is propylene-ethylene copolymer having a peak molecular weight Mp above 40,000 g/mol. The second copolymer may also be a metallocene-technology based propylene-ethylene copolymer. The second copolymer may in particular have a Mp in the range of from 50,000 g/mol to 130,000 g/mol, or from 60,000 g/mol to 110,000 g/mol.

The hotmelt composition may typically comprise from 10% to 70% by weight of the second copolymer, in particular from 20% to 60%, or from 30% to 50%. The second copolymer may be comprised of a single material as defined, as this simplifies the compounding and formulation of the hotmelt composition, but the second copolymer may also be a mixture of copolymers falling under this definition, as exemplified in Formula 2 below.

The second copolymer preferably comprises at least one copolymer, as described above, having an enthalpy of fusion, as measured according to the Enthalpy of Fusion Test Method described below, of at least 20 J/g, in particular from 25 J/g to 45 J/g. Polymer in this range can be described as semi-crystalline. The first copolymer may have a lower enthalpy of fusion, thus of less than 20 J/g, in particular from 5 J/g to 15 J/g, and may described as low-crystalline.

A commercial example of the second copolymer is Licocene® PP 3602 which is sold as granules and is described as a low crystalline metallocene-technology based propylene-ethylene copolymer. Another commercial example of the second copolymer is Licocene® PP 1602, also from Clariant, which is sold as granules and is described as a low melting, metallocene-technology based propylene-ethylene copolymer. Licocene® 3602 has a measured enthalpy of fusion of 35.0 J/g, while Licocene® 1622 has an enthalpy of fusion of 16.7 J/g.

The second propylene-ethylene copolymer having a peak molecular weight above 40,000 g/mol can provide good bond between two substrates. Blending a lower molecular weight first copolymer with the higher molecular weight, more crystalline, second copolymer was found to decrease the viscosity and "dilute" of the blend, making the composition more processable. Tackifier free formulations based on blends of low-crystalline and semi-crystalline propylene-ethylene copolymers have been found advantageous to provide good bond strength, particularly for NW—NW bonds.

An example is a blend of Licocene® 3602 and Licocene® 1302, which are propylene-ethylene copolymers from Clariant. Licocene 3602 is a relatively highly crystalline polymer, and also has a high viscosity. A blend of both (e.g. 50/50) can still maintain sufficient crystallinity but due to the presence of the lower molecular weight (Licocene 1302), the blend's viscosity is sufficiently low so that it can be applied at desired temperatures around 150-170° C.

This blending of the two different molecular weight propylene-ethylene copolymers was however found insufficient to stop the accretion of hotmelt material at the nozzle, leading to the "blobbing". However, the inventors found that such Licocene blends—as well as pure unblended Licocenes—have limitations in high speed convertibility via slot die nozzles.

Third Polymer

According to the invention, the inventors found that "blobbing" at high line speed for a blend of first and second copolymers can be effectively prevented when a small amount of another polymer having a high peak molecular weight Mp of from 70,000 g/mol to 700,000 g/mol, is used. The third polymer has a peak molecular weight which is at least greater by 10,000 g/mol than the peak molecular weight of the copolymer(s) of the second copolymer, in particular wherein the peak molecular weight of the third polymer is at least 20,000 g/mol or at least 50,000 g/mol higher than the second copolymer. The third polymer may in particular have a peak molecular weight of from 130,000 g/mol to 410,000 g/mol, or from 150,000 g/mol to 360,000 g/mol.

The third polymer may be a homopolymer or a copolymer. The third polymer may be a copolymers comprising different alpha olefin monomers such as ethylene, propylene, 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof.

The third polymer may be in particular a propylene-ethylene copolymer. The third polymer may be a metallocene-technology based copolymer, in particular a metallocene-technology based propylene-ethylene copolymer.

The third copolymer is preferably comprised of a single material as defined above, as this simplifies the compounding and formulation of the hotmelt composition, but the first copolymer may also be a blend of individual material falling under this definition. The hotmelt composition may comprise from 2% to 20% of such a third copolymer, by weight of the hotmelt composition, in particular from 5% to 15% by weight of the hotmelt composition.

Nonlimiting examples of commercially available third copolymer are Affinity EG 8200G, Engage 8200, Infuse 9817, Vistamaxx 3000, Vistamaxx 6102, Vistamaxx 6202, Vistamaxx 6502, VERsify 4200, VERsify 4301.

The third polymer may be a propylene-ethylene copolymer comprising greater than 80 wt. % of polypropylene units with isotactic stereochemistry. Examples of such copolymers are commercially available as the Vistamaxx series from ExxonMobil. For example, Vistamaxx 6202 and Vistamaxx 6502 are sold as pellets and are described by their manufacturer as primarily composed of isotactic propylene repeat units with random ethylene distribution, produced using a metallocene catalyst technology. Vistamaxx 6202 and 6502 were used as third polymer in the formula examples below.

Compounding and Optional Ingredients

The hotmelt composition can be prepared by heating the first, second and third polymers at a sufficiently elevated temperatures (e.g. about 135° C. to about 175° C.) to melt the polymers. One or more optional ingredients (e.g. additive or other polymers) can be added to this molten primary polymer blend. A mixer can be used to mix the polymers and other additives together into a final hotmelt composition.

The resulting blend is cooled and conditioned for transport and storage. During application, the hotmelt composition is molten again and can be applied to a substrate using any known applicator devices, in particular slot coating which is a contact applicator. The term "first", "second" and "third" (co)polymers are used to facilitate the designation of the copolymers in the claims and description, and do not necessarily reflect the relative proportion of the copolymers in the hotmelt composition or a particular order for compounding. However typically the third polymer may be present in the composition in lower amount than the first copolymer and/or the second copolymer.

The hotmelt composition according to the invention preferably has a viscosity at 170° C. is in the range from about 1,000 mPa s to about 7,000 mPa s, as measured according to the Viscosity Test Method as described herein.

While the hotmelt composition may comprise tackifiers, for example up to 30% by weight, one advantage of the present invention is that the amount of tackifiers may be substantially reduced compared to conventional adhesives. The hotmelt composition advantageously comprises less than 30% by weight of a tackifier. The hotmelt composition may in particular comprise less than 15% by weight of tackifiers, or be substantially free of tackifiers, which means comprising less than 5%, or less than 3%, or less than 2%, or less than 1%, by weight of the hotmelt composition, of a tackifier. The hotmelt composition can also be completely free of a tackifier, comprising 0% tackifier.

Exemplary tackifiers include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpenes, aromatic modified poly-terpenes, terpene-phenolics, aromatic modified hydrogenated poly-cyclopentadiene resins, hydrogenated aliphatic resins, hydrogenated aliphatic aromatic resins, hydrogenated terpenes and modified terpenes, and hydrogenated rosin esters.

There are significant advantages to minimizing or avoiding the use of a tackifier. This can reduce the cost of the hotmelt composition, as well as eliminate an additional ingredient and potential issues that may be associated with supplying the additional ingredient. Furthermore, tackifiers may impart undesirable odor in disposable articles and can also act as carriers of low molecular weight plasticizers (e.g., process oils that are used in SBC based adhesives) that may weaken the polyethylene back sheet materials used in absorbent articles and textile articles.

The hotmelt composition may optionally comprise an antioxidant. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetrakis[(methylene(3,5-di-t-butyl-4-hydroxyhydrocinnamate)]methane (e.g., IRGANOX™ 1010, from Ciba Geigy, New York); octadecyl-3,5-di-t-butyl-4-hydroxycinnamate (e.g., IRGANOX™ 1076, commercially available from Ciba Geigy) and combinations thereof. When used, the amount of the antioxidant in the hotmelt composition can be respectively less than 1%, alternatively from about 0.05% to about 0.75%, and alternatively from about 0.1% to about 0.5%, by weight of the hotmelt composition.

The hotmelt composition may optionally comprise a UV stabilizer that may prevent or reduce the degradation of the composition by radiation. Any UV stabilizer known to a person of ordinary skill in the art may be used in the hotmelt composition. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds, and combinations thereof. Where used, the amount of the UV stabilizer in the hotmelt composition can be less than 1%, alternatively from about 0.05% to about 0.75%, and alternatively from about 0.1% to about 0.5%, by weight of the hotmelt composition.

The hotmelt composition may optionally comprise a brightener, colorant, and/or pigment. Any colorant or pigment known to a person of ordinary skill in the art may be used in the hotmelt composition. Non-limiting examples of suitable brighteners, colorants, and/or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant, and/or pigment in the hotmelt composition can be less than 10%, alternatively from about 0.01% to about 5%, and alternatively from about 0.1% to about 2%, by weight of the hotmelt composition.

The hotmelt composition may optionally comprise a fragrance such as a perfume or other odorant. Such fragrances may be retained by a liner or contained in release agents such as microcapsules that may, for example, release fragrance upon removal of a release liner from or compression on the adhesive composition. Where used, the amount of the fragrance in the hotmelt composition can be less than 3%, alternatively less than 2%, alternatively less than 1%, alternatively from about 0.05% to about 0.75%, and alternatively from about 0.1% to about 0.5%, by weight of the hotmelt composition.

Examples & Data

Table 1 discloses the peak molecular weight (Mp) in g/mol of some commercially available polymers that may be used in invention.

TABLE 1

|   | Mp |
| --- | --- |
| Licocene 1302 | 24,100 |
| Licocene 1602 | 75,900 |
| Licocene 3602 | 80,000 [1] |
| Vistamaxx 3000 | 299,500 |
| Vistamaxx 6102 | 687,700 [1] |
| Vistamaxx 6202 | 330,800 [1] |
| Vistamaxx 6502 | 185,300 |

[1] correlated (not measured directly)

Table 2 below shows two exemplary formulations using some of the copolymers listed above. All percentages are by weight of the composition.

TABLE 2

|   | Formula 1 | Formula 2 |
| --- | --- | --- |
| Copolymer 1 | 50% Licocene 1302 | 50% Licocene 1302 |
| Copolymer 2 | 30% Licocene 3602 + 10% Licocene 1602 | 40% Licocene 3602 |
| Copolymer 3 | 10% Vistamaxx 6202 | 10% Vistamaxx 6502 |

These formulas can be used as hotmelt composition for nonwoven-nonwoven as well as nonwoven-film applications. Both Formula 1 and Formula 2 were tested as slot coating application on a nonwoven at high speed (>4 m/s). The two formulations of the invention showed no blobbing, also after run times of up to 10 min at high speed.

In contrast, a pure Licocene® like e.g. 2502, 1602 or 1502, which has low enough viscosity, or a blend of Licocenes® (like e.g. 3602 and 1302), in which a lower molecular weight Licocene® like 1302 is used to decrease the otherwise too high viscosity Licocene® like 3602, shows blobbing after run times of only 1 to 3 minutes.

While not wishing to be bound by theory, the inventors believe that the blobbing observed when using pure polymer compositions of the type disclosed in the prior art is related to a viscoelastic response to shear and resulting normal forces in the polymer. The inventors believe that having two different polymer molecular weights, sufficiently different from each other in magnitude, will cause one to lubricate the other in shear. This is realized in the present invention by having the third polymer with a peak molecular weight of at least 10,000 g/mol greater than the second copolymer's peak molecular weight. Thus adding the third copolymer having a high Mp alleviates the issue of slot coat blobbing of the second copolymer. In order to keep the overall viscosity of the hotmelt composition processable, it was found that the first copolymer having a lower peak molecular weight should be added to the formulation.

Formula 1 and formula 2 were respectively slot coated at a basis weight of 7.8 gsm on a first nonwoven substrate, and a second nonwoven substrate was pressed against the coated side of the first nonwoven substrate to make a bond. The bond strength measured as the time it takes to delaminate both nonwoven with a weight 150 gsm was found very good, both at initial conditions and accelerated aging (15 days at 60° C.). A comparative tackifier free adhesive comprising a blend of an amorphous polyalphaolefins (APOA) (Rextac® 2830) and a propylene-ethylene copolymer (Licocene® 6502) was found to have a much lower bond strength as the invention examples.

General Description of an Absorbent Article

"Absorbent article", as used herein, refers to personal hygiene products that are placed against or in proximity to the body of the wearer to absorb and contain the various exudates discharged from the body. Absorbent articles include baby diapers, training pants, adult incontinence undergarments, feminine hygiene products, and the like. As used herein, the term "body fluids" or "body exudates" includes, but is not limited to, urine, blood, vaginal discharges and fecal matter.

Figure 2:
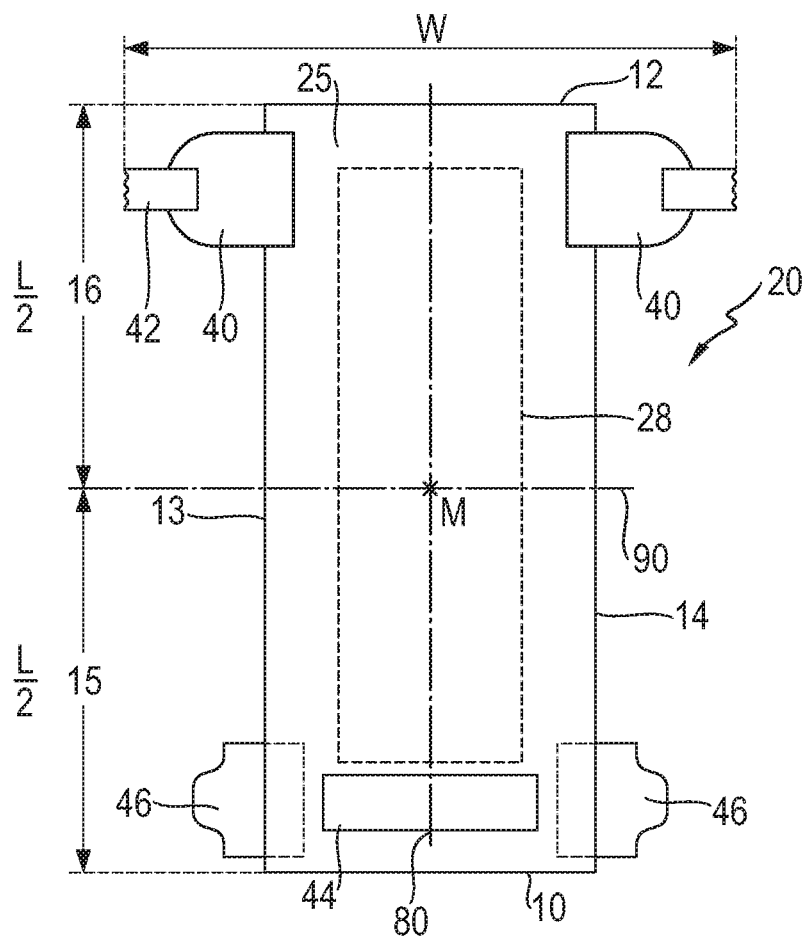
FIG. 2 shows the garment-facing side of the diaper of FIG. 1 with the diaper flattened out.
Figure 3:
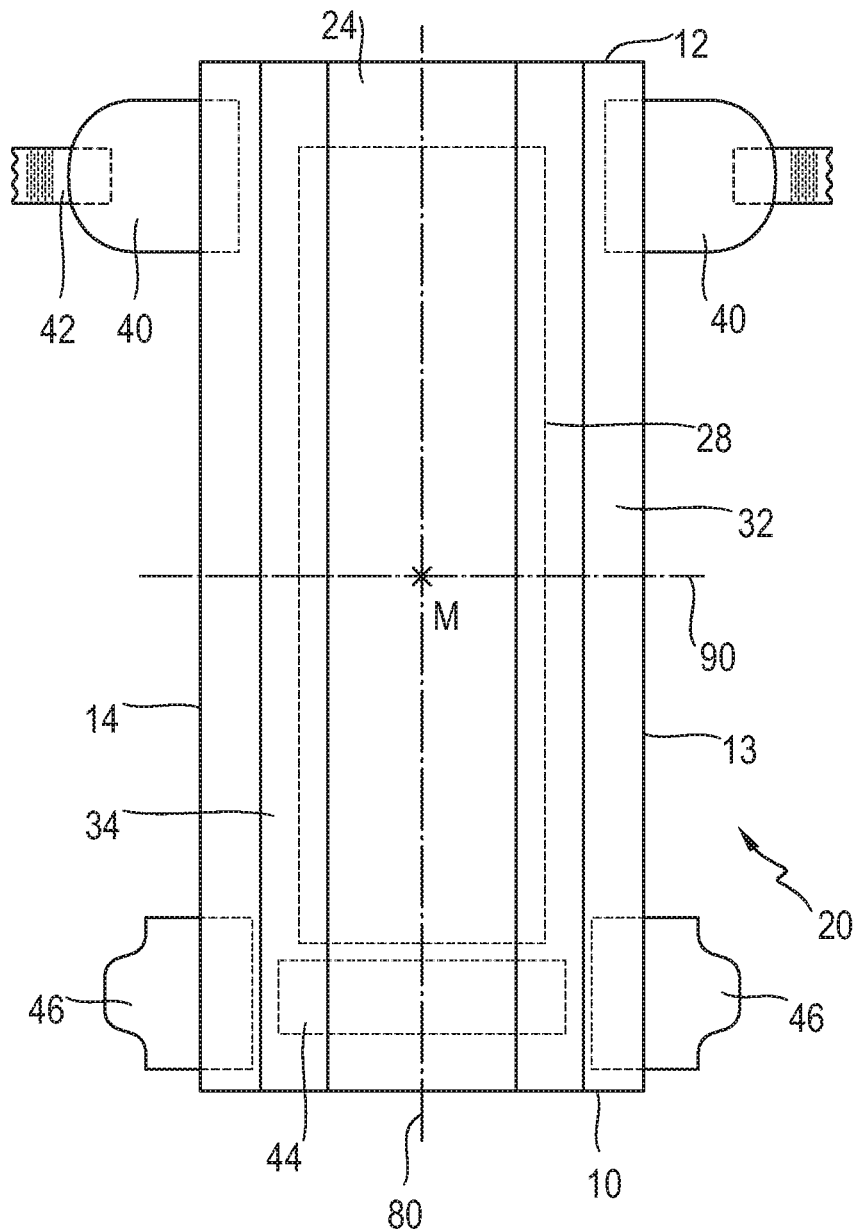
FIG. 3 shows the wearer-facing side of the diaper of FIG. 1 with the diaper flattened out.

An exemplary absorbent article according to the invention in the form of a baby taped diaper 20 is represented in FIGS. 1-3. FIG. 1 is a perspective view of the exemplary diaper in a closed state as it would appear when worn by a wearer. This taped diaper 20 is shown for illustration purpose only as the invention may be used for making a wide variety of diapers or other absorbent articles such as baby diaper pants, adult incontinence pants or feminine sanitary pads. In the following, the word "diaper" and "absorbent article" are used interchangeably. The Figures are used herein as illustration of one way to carry out the invention and are not limiting the scope of the claims, unless specifically indicated to do so. The taped diaper 20 may have a transverse axis 90 and a longitudinal axis 80. The transverse axis 90 extends perpendicular to the longitudinal axis 80.

The absorbent article comprises a liquid permeable topsheet 24 on its wearer-facing surface, a liquid impermeable backsheet 25 on its garment-facing surface and an absorbent core 28 between the topsheet and the backsheet (shown in dotted line in FIGS. 2 and 3). The topsheet typically forms the majority of the wearer-contacting surface of the article and is the first layer that the body exudates contact. The topsheet is liquid permeable, permitting liquids to readily penetrate through its thickness. Any known topsheet may be used in the present invention. The backsheet typically comprises a fluid impermeable plastic film, which may be printed with a backsheet pattern, and a low basis weight nonwoven outer cover glued to this impermeable film to give a nicer feel and appearance to the backsheet.

The absorbent article may also typically comprise a fluid acquisition layer and/or a fluid distribution layer between the topsheet and the absorbent core, which is not represented in the Figures for simplicity but are present in most diapers, as well as outer barrier cuffs 32 and inner barrier cuffs 34, as is known in the art. The absorbent article may also comprise other usual components if it is desired to increase the performance of the article, such as transverse barrier cuffs, front and/or back elastic waistbands, a lotion application on the topsheet, longitudinally extending channels in the core and/or the distribution layer, a wetness indicator, etc. all these components have been extensively described and exemplified in the art. More detailed disclosures of example of such components are for example disclosed in WO 2014/93323, WO 2015/183669 (both Bianchi et al.), WO 2015/031225 (Roe et al.) or WO 2016/133712 (Ehrnsperger et al.) to name a few.

The absorbent article typically comprises a front edge 10, a back edge 12, and two longitudinally-extending side (lateral) edges 13, 14. The front edge 10 is the edge of the article which is intended to be placed towards the front of the user when worn, and the back edge 12 is the opposite edge, and together form the waist opening of the diaper. The lateral edges 13, 14 respectively form the two leg openings. The topsheet 24, the backsheet 25, the absorbent core 28 and the other article components may be assembled in a variety of well-known configurations, in particular by gluing, fusion and/or pressure bonding. The absorbent articles of the invention may comprise any typical layers and components used in absorbent products of the diaper type, and which are not necessarily represented in the simplified FIGS. 1-3. A plurality of absorbent articles may be packaged together in a package.

General Description of an Absorbent Core

"Absorbent core" means an absorbent structure disposed between topsheet and backsheet for absorbing and containing liquid such as urine received by the absorbent article. The absorbent core comprises an absorbent material, that is typically enclosed within or sandwiched between a core wrap. The core wrap may be a single material that is folded and attached to itself, or it may comprise a separate top layer and bottom layer that are bonded together. The absorbent material typically comprises superabsorbent particles which are optionally mixed with cellulose fibers. As used herein, "absorbent core" does not include any acquisition-distribution systems, topsheet, or backsheet of the absorbent article.

Figure 4:
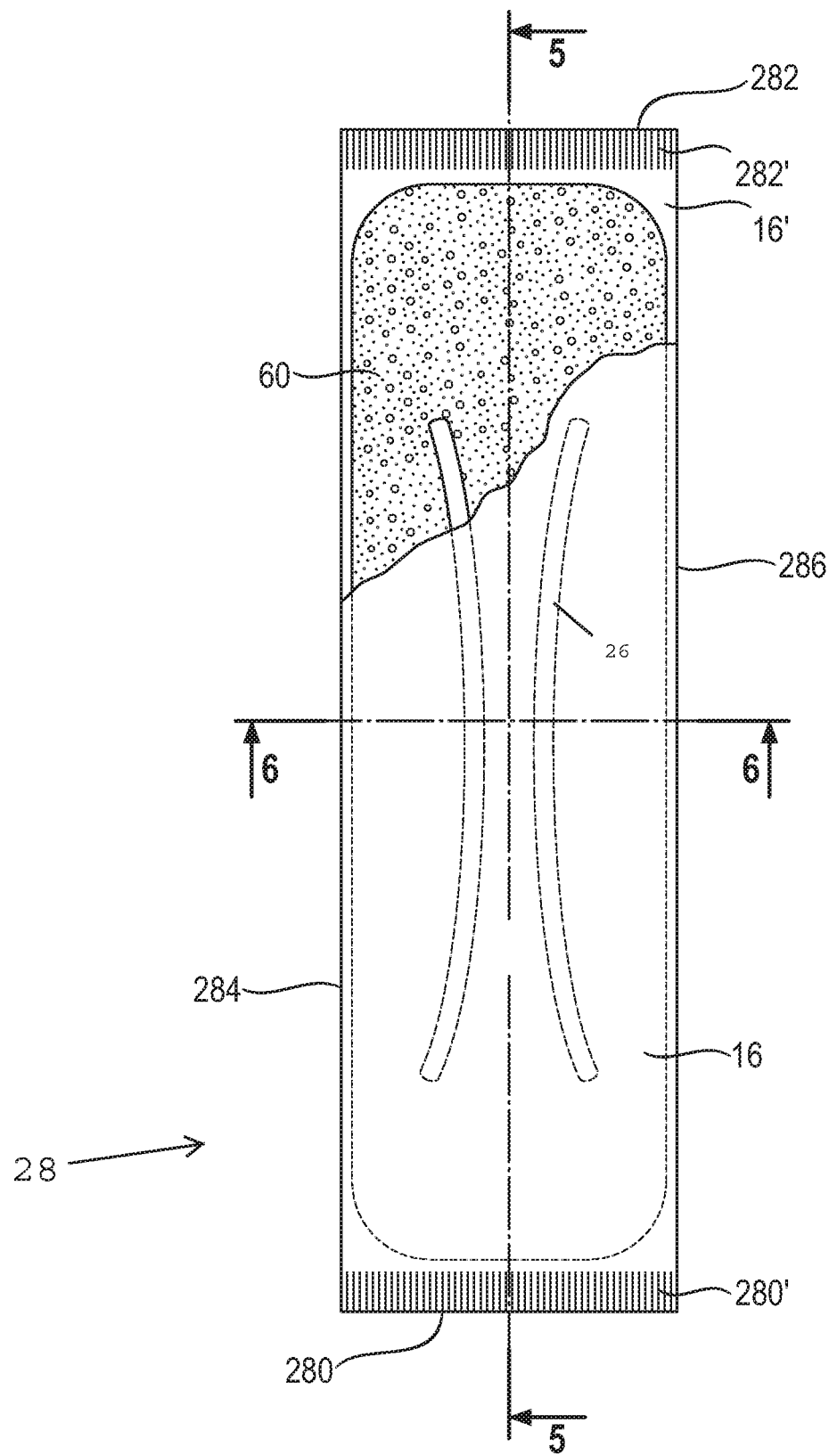
FIG. 4 shows a top view of an exemplary absorbent core with the top layer partially removed.

The absorbent core 28 is the component of the absorbent article having the most absorbent capacity. An exemplary absorbent core 28 is shown in isolation in FIGS. 4-6, in dry state (before use). The absorbent core may typically have a generally rectangular shape as defined by the longitudinal edges 284, 286 and transversal front edge 280 and back edge 282. The absorbent core 28 comprises an absorbent material 60, deposited as a layer having a generally rectangular outline, as represented on FIG. 4. This absorbent core represented is of course not limiting the scope of the invention as the invention is applicable to a wide variety of absorbent cores. It is also common to have an absorbent material 60 layer having a non-rectangular outline ("shaped" core), in particular the absorbent material layer may define a tapering along its width towards the central region of the core (or "dog-bone" shape). In this way, the absorbent material deposition area may have a relatively narrow width in an area of the core intended to be placed in the crotch region of the absorbent article. This may provide for example better wearing comfort. Other shapes can also be used such as a "T" or "Y" or "sand-hour" for the area of the absorbent material.

The absorbent material 60 may be any conventional absorbent material known in the art. For example, the absorbent material may comprise a blend of cellulose fibers and superabsorbent particles ("SAP"), typically with the percentage of SAP ranging from about 50% to about 75% by weight of the absorbent material. The absorbent material may also be free of cellulose fibers, as is known in so-called airfelt-free cores where the absorbent material consists of SAP.

"Superabsorbent polymer" or "SAP" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of at least 20 g/g, in particular of from 20 g/g to 40 g/g. "Superabsorbent polymer particles", as used herein, refers to a superabsorbent polymer material which is in particulate form so as to be flowable in the dry state.

Various absorbent core designs comprising high amount of SAP have been proposed in the past, see for example in U.S. Pat. No. 5,599,335 (Goldman), EP 1,447,066 (Busam), WO 95/11652 (Tanzer), US 2008/0312622 A1 (Hundorf), WO 2012/052172 (Van Malderen). In particular the SAP printing technology as disclosed in US 2006/024433 (Blessing), US 2008/0312617 and US 2010/0051166 A1 (both to Hundorf et al.) may be used. The invention is however not limited to a particular type of absorbent core. The absorbent core may also comprise one or more glue such as an auxiliary glue applied between the internal surface of one (or both) of the core wrap layers and the absorbent material to reduce leakage of SAP outside the core wrap. A microfibrous adhesive net may also be used in air-felt free cores as described in the above Hundorf references. These glues are not represented in the Figures for simplicity.

The absorbent material may be deposited as a continuous layer within the core wrap. The absorbent material may also be present discontinuously for example as individual pockets or stripes of absorbent material enclosed within the core wrap and separated from each other by material-free junction areas. A continuous layer of absorbent material, in particular of SAP, may also be obtained by combining two absorbent layers having matching discontinuous absorbent material application pattern wherein the resulting layer is substantially continuously distributed across the absorbent particulate polymer material area. As for example taught in US 2008/0312622 A1 (Hundorf), each absorbent material layer may thus comprise a pattern having absorbent material land areas and absorbent material-free junction areas, wherein the absorbent material land areas of the first layer correspond substantially to the absorbent material-free junction areas of the second layer and vice versa.

The basis weight (amount deposited per unit of surface) of the absorbent material may also be varied to create a profiled distribution of absorbent material, in particular in the longitudinal direction (as schematically illustrated in FIG. 5) to provide more absorbency towards the center and the middle of the core, but also in the transversal direction, or both directions of the core. The absorbent core may also comprise longitudinally extending channels which are substantially free of absorbent material within the absorbent material area. The core wrap may be bonded through these material-free areas. Exemplary disclosures of such channels in an airfelt-free core can be found in WO 2012/170778 (Rosati et al.) and US 2012/0312491 (Jackels). Channels may of course also be formed in absorbent cores comprising cellulose fibers.

Core Wrap

The function of the core wrap is to contain the absorbent material. As indicated in the background, different core wrap constructions can be used. A typical core wrap construction comprises two nonwoven substrates 16, 16', which are attached to another and form respectively the top layer 16 and the bottom layer of the core wrap 16'. These two layers may be typically attached to another along at least part of the periphery of the absorbent core to form a seal. Typically, neither the first nor the second substrate needs to be shaped, so that they can be rectangularly cut for ease of production, but other shapes are not excluded. The terms "seal" is to be understood in a broad sense. The seal does not need to be continuous along the whole periphery of the core wrap but may be discontinuous along part or the whole of it, such as formed by a series of seal points spaced on a line. Typically, a seal may be formed by gluing and/or thermal bonding.

The core wrap represented in the Figures comprises a top layer 16 which is wider than the bottom layer 16' so that two flaps of the top layer can be folded over the bottom layer along the longitudinal edges 284, 286 of the core respectively to which they are attached, typically by an adhesive to form the longitudinal seals 284', 286'. The front edge 280 and back edge 282 may also be sealed, for example by a sandwich seal 280', 282'. Such transversal seals may for example made by adhesive stripes applied in machine direction by the slot glue technique, as is known in the art. Alternatively, is it possible to leave the transversal edges 280, 282 open without a seal. For example, there may be enough core wrap material between the edges of the core and the absorbent material 60 to provide a buffer zone at these ends.

The invention is applicable to any of these core wrap seals as well as the core channel bonds 27 that will be discussed further below Alternatively, the core wrap may be made of a single piece of nonwoven which has been folded over itself around the absorbent material layer 60, and is bonded to itself along a single longitudinal seal, instead of two longitudinal seals 284' and 286' as represented in the Figures. The invention is also applicable to such a core wrap.

The top layer 16 and the bottom layer 16' may be made from the same base substrate material which has been differently treated. Such nonwoven substrate may have a basis weight within a range of from about 8 to about 12 gsm. The top layer may be typically a nonwoven layer made of synthetic fibers that has been treated with a surfactant to increase its hydrophilicity. Both layers may in particular each comprises or consists of a nonwoven web, such as a carded nonwoven, a spunbond nonwoven ("S") or a melt-blown nonwoven ("M"), and a multi-layer of any of these. For example, spunbond/meltblown laminate (spunmelt) polypropylene nonwovens are commonly used and are particularly suitable, especially those having a multi-layer SMS, or SMMS, or SSMMS, structure. Examples are disclosed in U.S. Pat. No. 7,744,576, US 2011/0268932 A1, US 2011/0319848 A1 or US 2011/0250413 A1. Typical material used to make the synthetic fibers are PE (polyethylene), PET (polyethylene terephthalate) and in particular PP (polypropylene).

Spunbond, also called spunlaid, nonwovens are made in one continuous process. Fibers are spun through a number of small orifices in a spinneret to form fibers or filaments, which are then directly dispersed into a web by deflectors or can be directed with air streams on a moving foraminous surface, such as a wire mesh conveyor. Meltblown nonwovens are produced by extruding melted polymer fibers through a spinneret or die consisting of up to 40 holes per inch to form long thin fibers which are stretched and cooled by passing hot air over the fibers as they fall from the die. The diameters of the fiber are significantly reduced by hot air which also breaks the continuous filaments into microfibers of varying length to diameter ratio. The extremely fine fibers (typically polypropylene) differ from other extrusions, particularly spunbond, in that they have low intrinsic strength but much smaller size offering key properties.

The spunbond process can be combined with the meltblown process to form a multi-layer web having S (spunbond) layer and M (meltblown) layer, in particular SM, SMS or SMMS webs, which are strong and offer the intrinsic benefits of fine fibers. The nonwovens may be consolidated using known techniques, typically thermal point bonding. In thermal point bonding, heat is applied locally on individual regions of the nonwoven to locally melt and fuse the fibers together. Fusion bond patterns are for example disclosed in US 2011/0250413 (Hu et al. should be Lu) and US 2014/0072767 A1 (Klaska et al.). The resultant web is typically collected into rolls at the supplier and subsequently converted to finished products.

Core Channels

The absorbent core 28 may comprise one or more channels 26, in particular at least one channel on each side of the core's longitudinal centerline, which may or may not be connected and are present within the absorbent material layer. The channels may in particular be areas substantially free of absorbent material, in particular areas completely free of absorbent material (accidental minute amount of absorbent material due to involuntary contamination of the channels due to the high speed of the making process being disregarded).

The channels 26 may comprise a channel bond 27 between the top side 16 of the core wrap and the bottom side 16' of the core wrap. This bond 27 provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive may be for example applied in the areas of the channels on the inner side of the top side and/or the inner side of the bottom side of the core wrap, typically by slot glue application or any other means, followed by the application of pressure in the areas of the channels to provide a good adhesive bonding in these areas. Exemplary patent disclosures of such adhesive bonding processes can be found for an airfelt or airfelt-free absorbent cores in WO 2012/170798 A1 (Jackels et al.), EP 2,905,000 (Jackels) and EP 2,905,001 (Armstrong-Ostle et al.).

The hotmelt composition of the invention may be particularly useful to make these channel bonds 27, in addition or alternatively to the core perimeter bonds 280'-286'. Typically, the bonds 27 may generally have the same outline and shape as the channel areas 26 in which they are contained, but may be slightly smaller to allow for a safety margin (e.g. by a few mm) as some deviations from the optimal registration may happen during high speed process. It is expected that the channel bonds 27 may be more efficiently made and stronger if they are provided in macroscopic areas with no absorbent material (except of course accidental contamination) compared to bonds provided in areas containing non-negligible absorbent material.

Pant Diaper

The absorbent article may also be in the form of a pant having permanent or refastenable side seams, which is not represented herein but for which the invention may also apply. Pant articles comprising refastenable seams are for example disclosed in US 2014/0005020 and U.S. Pat. No. 9,421,137. Typical pant articles comprise a chassis (sometimes referred to as a central chassis or central panel) comprising a topsheet, a backsheet, and an absorbent core, which may be as disclosed herein, and a front belt that defines a front waist region and a back belt that defines a back waist region. The chassis may be joined to a wearer-facing surface of the front and back belts or to a garment-facing surface of the belts. Side edges of the front belt may be joined to side edges of the back belt to form two side seams. The side seams may be any suitable seams known to those of skill in the art, such as butt seams or overlap seams, for example. When the side seams are permanently formed or refastenably closed, the absorbent article in the form of a pant has two leg openings and a waist opening circumference. The side seams may be permanently joined using adhesives or bonds, for example, or may be refastenably closed using hook and loop fasteners, for example.

Alternatively, instead of attaching belts to the chassis to form a pant, discrete side panels may be attached to side edges of the chassis. Suitable forms of pants comprising discrete side panels are e.g. disclosed e.g. in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Backsheet

The backsheet 25 is the liquid impermeable layer that generally form the garment-facing side of the absorbent article. The backsheet 25 prevents, or at least inhibits, the bodily exudates absorbed and contained in the absorbent core 10 from soiling articles such as bedsheets, undergarments, and/or clothing. The backsheet typically comprises a liquid impermeable, or at least substantially liquid impermeable layer, such as a thin plastic film e.g. having a thickness of about 0.012 mm to about 0.051 mm. Suitable backsheet materials also include breathable materials which permit vapors to escape from the absorbent article, while still preventing, or at least inhibiting, bodily exudates from passing through the backsheet.

The backsheet 25 typically further comprises on its external side a nonwoven outer cover for improving the overall feel of the backsheet. The outer cover material (sometimes referred to as a backsheet nonwoven) is typically a nonwoven material joined to and covering the backsheet film. Thus the outer cover material typically forms at least a portion of the garment-facing surface of the absorbent article 20. The outer cover material may comprise a bond pattern, apertures, and/or three-dimensional features.

Landing Zone

Referring to FIGS. 1 and 2, the absorbent article 20 in the form of a taped diaper may have a discrete landing zone 44 on its garment-facing side, typically disposed proximate the front edge 10 of the article 20. The landing zone 44 is configured to receive the fasteners 42 and may comprise, for example, a plurality of loops configured to be engaged with, a plurality of hooks on the fasteners 46, or vice versa.

The landing zone 44 typically comprises one or more discrete nonwoven materials that are attached to a portion of the outer cover material 40 in the front waist region 12. The present invention is in particular applicable to the bond area between such a landing zone 44 and the backsheet outer cover 25.

Bond Areas

The absorbent article comprises at least a bond area between a first substrate and a second substrate provided by the hotmelt composition. A hotmelt composition according to the invention is disposed within the bond area. The bond area may be continuous or discontinuous. The hotmelt composition is applied in molten state to a first substrate, the second substrate being placed in contact with the deposited hotmelt and pressure is applied before the hotmelt solidifies on the two substrates to ensure that bonding takes place.

The hotmelt composition may be the only bonding means holding the first substrate and the second substrate bonded together within the bond area. Alternatively, the hotmelt composition may be supplemented by another bonding means, such as mechanical bonds or fusion bonds. However, it is preferred that the bonding area is free of conventional hotmelt adhesive which comprises a substantial amount of tackifier, e.g. more than 30% by weight of tackifiers.

The present invention is applicable to any pair of non-wovens of the articles. "Nonwoven", as used herein, is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to greater than 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm of $g/m^2$). Typical nonwovens that may be used in the invention have a basis weight in the range of about 5 gsm to about 50 gsm, or up to about 40 gsm for example.

In particular, the first nonwoven material and the second nonwoven material bonded by the hotmelt composition of the invention may be the top layer 16 and bottom layer 16' of the core wrap respectively. The hotmelt composition may thus form the core wrap end seals 280', 282', and/or longitudinal seals 284', 286' and/or channel bonds 27. The first nonwoven and second nonwoven may also be the landing zone 40 and the nonwoven outer cover of the backsheet 25.

The hotmelt composition is also useful to bond film and nonwoven, for example for bonding the front ear to the liquid-impermeable polymer film of the backsheet. The hotmelt composition may be applied to the nonwoven for this NW-film application, or vice versa.

Other nonwovens in the article that may be bonded in the present invention may be selected in the group consisting of the liquid permeable topsheet 24, the barrier leg cuff material 32-34, any nonwoven waist bands (not shown), an acquisition material or secondary top sheet, or any other nonwoven materials.

The hotmelt composition may be typically present at a basis weight ranging from about 5 gsm to about 30 gsm within the bond area, alternatively from about 8 gsm to about 25 gsm. The first and/or the second nonwoven material may comprise natural or recycled fibers.

It may be that the adhesive is applied in a way that the bond area is not uniformly covered with the adhesive but there can e.g. be parts of the bond area which are free of adhesive, e.g. if the adhesive has been applied in stripes by using a slot coating nozzle with a comb shim. In such cases, the basis weight of the adhesive is defined as the average basis weight of the adhesive over the bond area. Typical stripes widths are 1 mm wide separated by 1 mm gap, but of course this is not limiting of the invention.

The hotmelt composition may be applied in the slot coating process on the first or the second substrate or both substrates preferably at a line speed of more than 2 m/s, in particular of more than 3 m/s, or even of more than 4 m/s.

Test Methods

Peak Molecular Weight (Mp) Measurement Method

The peak molecular weight is determined using a gel permeation chromatography (GPC) method. GPC is a well-known method wherein polymers are separated according to molecular size, the largest molecule eluting first. The peak molecular weights referred to herein can be determined with gel permeation chromatography (GPC) using polystyrene calibration standards, such as is done according to ASTM D5296. The molecular weight of any polymer or unknown polymer measured using GPC so calibrated is the styrene equivalent molecular weight, which herein is defined as the "peak molecular weight." Suitable solvents and temperatures are employed with GPC in order to achieve adequate molecular weight separation and resolution.

Enthalpy of Fusion Test Method

The Enthalpy of Fusion Parameter of a hot melt adhesive composition is determined using the Enthalpy of Fusion Test Method, which consists of performing ASTM D3418-15 with the following additional guidance. Specimen(s) are preferably extracted from molded or pelleted raw material adhesive composition. If raw material is not available, specimen(s) of adhesive are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of fusion is calculated as specified in section 11.4 based on the curve corresponding to decreasing temperature (at 1° C./min) and is reported as the "Enthalpy of Fusion" in units of joules per gram (J/g) to the nearest 0.1 J/g.

Viscosity Test Method

The Viscosity Parameter of a hot melt adhesive composition is determined using the Viscosity Parameter Test Method, which consists of performing ASTM D3236-15 with the following additional guidance. A Brookfield RVT viscometer with spindle SC 4-27 (Brookfield Engineering, Middleboro, MA, USA), or equivalent, is used. The sample temperature is maintained at 170.0±1.0° C., unless otherwise specified, throughout the measurement. The sample is preheated for 10 minutes and stirred with the measurement spindle for 30 min. The spindle is rotated at 20 rpm throughout the measurement. The resulting apparent viscosity, as described in section 10, is reported as the "viscosity" in units of millipascal-seconds to the nearest 100 mPa-s.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A hotmelt composition comprising:
   from 30% to about 70% of a first polymer or mixture of polymers having a peak molecular weight below 40,000 g/mol;
   from about 10% to about 70% of a second polymer or mixture of polymers having a peak molecular weight above 40,000 g/mol; and
   from about 2% to about 20% of a third polymer or mixture of polymers having a peak molecular weight of from about 70,000 g/mol to about 700,000 g/mol, wherein the peak molecular weight of the third polymer or mixture of polymers is greater than the peak molecular weight of the second polymer or mixture of polymers by at least 10,000 g/mol.

2. The hotmelt composition according to claim 1, comprising by weight of the hotmelt composition:
   from about 40% to about 60% of the first polymer or mixture of polymers;
   from about 30% to about 50% of the second polymer or mixture of polymers; and
   from about 5% to about 15% of the third polymer or mixture of polymers.

3. An absorbent article comprising a first substrate and a second substrate, wherein the first substrate and the second substrate are at least partially bonded by the hotmelt composition according to claim 1, and wherein either a) the first substrate is a first nonwoven and the second substrate is a second nonwoven or b) the first substrate is a nonwoven and the second substrate is a plastic film.

4. A package comprising a plurality of the absorbent articles according to claim 3.

5. A process for bonding a first substrate to a second substrate, the process comprising the step of applying the hotmelt composition according to claim 1 on the first substrate and/or the second substrate by a contact applicator and pressing the two substrates together before the hotmelt composition solidifies to create a bond between the two substrates, wherein the hotmelt composition is applied on the first substrate and/or the second substrate at a line speed of more than 2 m/s.

6. A hotmelt composition comprising:
from 30% to about 70% of a first propylene-ethylene copolymer having a peak molecular weight below 40,000 g/mol;
from about 10% to about 70% of a second propylene-ethylene copolymer having a peak molecular weight above 40,000 g/mol; and
from about 2% to about 20% of a third polymer or mixture of polymers having a peak molecular weight of from about 70,000 g/mol to about 700,000 g/mol, wherein the peak molecular weight of the third polymer or mixture of polymers is greater than the peak molecular weight of the second copolymer by at least 10,000 g/mol;
wherein the peak molecular weight is measured according to the Peak Molecular Weight Measurement Method.

7. The hotmelt composition according to claim 6, wherein the first propylene-ethylene copolymer has a peak molecular weight ranging from about 4,000 g/mol to about 31,000 g/mol.

8. The hotmelt composition according to claim 6, wherein the second propylene-ethylene copolymer has a peak molecular weight ranging from about 50,000 g/mol to about 130,000 g/mol.

9. The hotmelt composition according to claim 6, wherein the third polymer or mixture of polymers is a propylene-ethylene copolymer comprising greater than 80% by weight of polypropylene units.

10. The hotmelt composition according to claim 9, wherein the third propylene-ethylene copolymer has a peak molecular weight ranging from about 130,000 g/mol to about 410,000 g/mol.

11. The hotmelt composition according to claim 6, wherein at least one selected from the first propylene-ethylene copolymer, the second propylene-ethylene copolymer, and third polymer or mixture of polymers is a metallocene-technology based propylene-ethylene copolymer.

12. The hotmelt composition according to claim 6, wherein the hotmelt composition comprises from about 0% to less than 30% by weight of a tackifier.

13. The hotmelt composition according to claim 6, wherein the second propylene-ethylene copolymer has an enthalpy of fusion of from about 25 J/g to about 45 J/g, and the first propylene-ethylene copolymer has an enthalpy of fusion of from about 5 J/g to about 15 J/g, as measured according to the Enthalpy of Fusion Test Method.

14. The hotmelt composition according to claim 6, wherein the viscosity of the hotmelt composition at 170° C. is in the range from about 1,000 mPa·s to about 7,000 mPa·s, as measured according to the Viscosity Test Method.

15. An absorbent article comprising a first substrate and a second substrate, wherein the first substrate and the second substrate are at least partially bonded by the hotmelt composition according to claim 6, and wherein either a) the first substrate is a first nonwoven and the second substrate is a second nonwoven or b) the first substrate is a nonwoven and the second substrate is a plastic film.

16. A package comprising a plurality of the absorbent articles according to claim 15.

17. A process for bonding a first substrate to a second substrate, the process comprising the step of applying the hotmelt composition according to claim 6 on the first substrate and/or the second substrate by a contact applicator and pressing the two substrates together before the hotmelt composition solidifies to create a bond between the two substrates, wherein the hotmelt composition is applied on the first substrate and/or the second substrate at a line speed of more than 2 m/s.

* * * * *